United States Patent [19]
Silvestri et al.

[11] 3,941,773
[45] Mar. 2, 1976

[54] FORM II AMPICILLIN
[75] Inventors: Herbert H. Silvestri, DeWitt; David A. Johnson, Fayetteville, both of N.Y.
[73] Assignee: Bristol-Myers Company, New York, N.Y.
[22] Filed: Nov. 2, 1964
[21] Appl. No.: 408,191

Related U.S. Application Data
[63] Continuation-in-part of Ser. No. 233,943, Oct. 29, 1962, Pat. No. 3,180,862.

[52] U.S. Cl................................. 260/239.1; 424/271
[51] Int. Cl.²........................................ C07D 499/44
[58] Field of Search................................ 260/239.1

[56] References Cited
UNITED STATES PATENTS
3,144,445    8/1964    Grant et al...................... 260/239.1

*Primary Examiner*—Nicholas S. Rizzo
*Attorney, Agent, or Firm*—Richard H. Brink

EXEMPLARY CLAIM

1. A new crystalline form of D-6-(2-amino-2-phenyl-acetamido)penicillanic acid characterized by being substantially free of water in the chemically bound state, having a molecular weight of about 349, having an infrared spectrograph as disclosed in FIG. 1 of the drawings, and possessing substantially greater storage stability than hydrated crystalline D-6-(2-amino-2-phenyl-acetamido)penicillanic acid.

2 Claims, 2 Drawing Figures

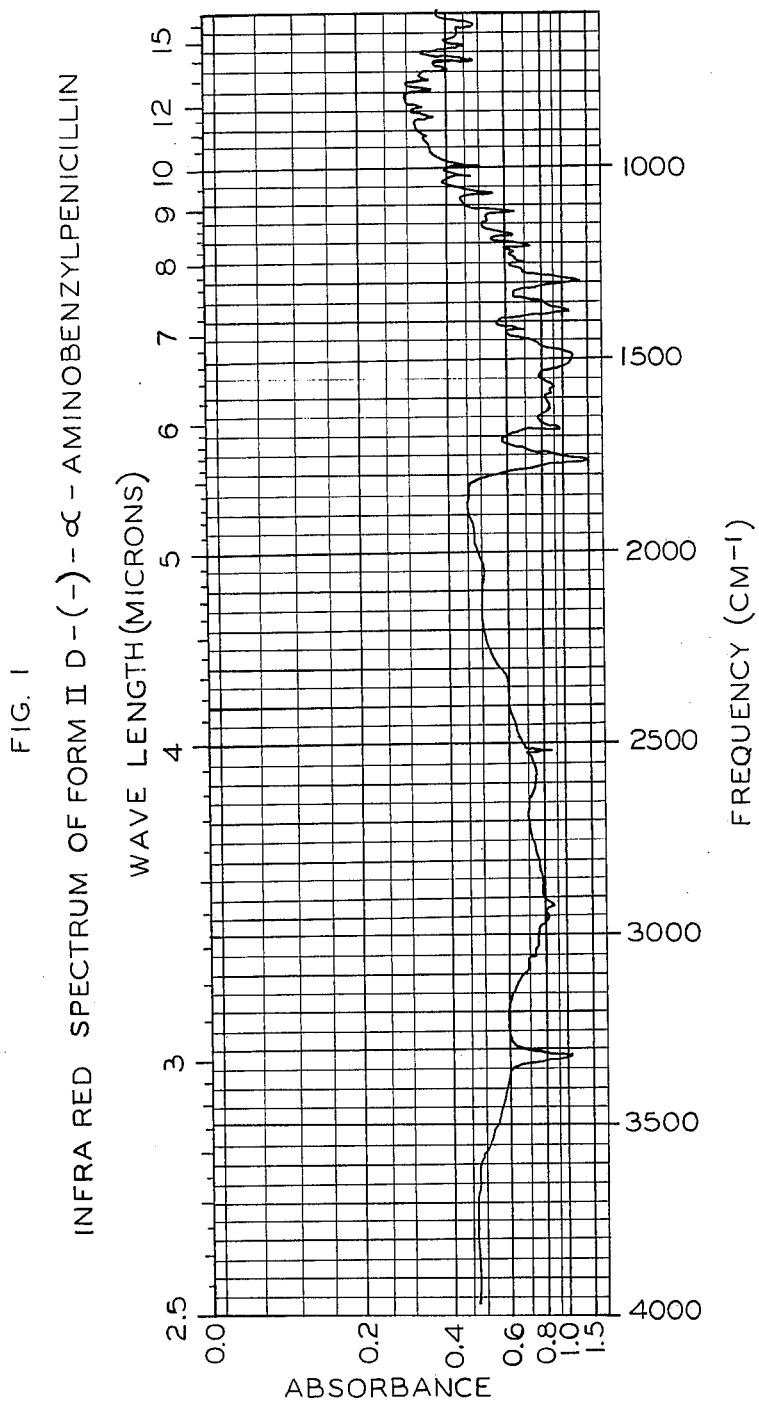

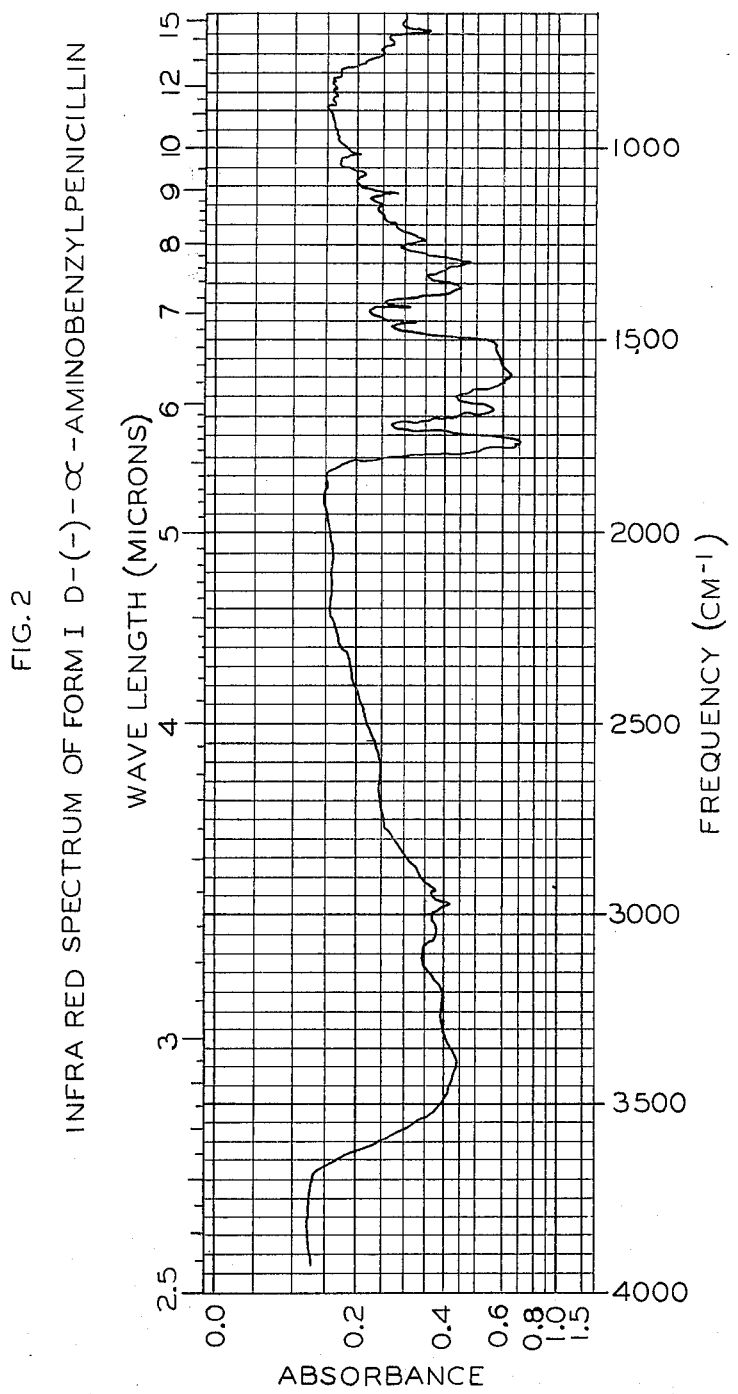

FORM II AMPICILLIN

This application is a continuation-in-part of our prior, co-pending application Ser. No. 233,943, filed Oct. 29, 1962, now U.S. Pat. No. 3,180,862.

This invention relates to a new form of D-(—)-α-aminobenzylpenicillin of value as an antibacterial agent, as a nutritional supplement in animal feeds, as an agent for the treatment of mastitis in cattle, as a therapeutic agent in poultry and animals, including man, and especially in the treatment of infectious diseases caused by Gram-positive and Gram-negative bacteria. More particularly, this invention relates to a novel, stable crystalline form of D-(—)-α-aminobenzylpenicillin designated as Form II D-(—)-α-aminobenzylpenicillin or Form II ampicillin which is characterized by being substantially free of water in the chemically bound state, and by exhibiting an infrared absorption spectrum substantially as disclosed in FIG. 1 of the drawings.

Subsequent to the making of the invention described and claimed herein, it was discovered by our colleagues, David A. Johnson and Glenn A. Hardcastle, Jr., as disclosed in U.S. Ser. No. 266,807, filed Mar. 21, 1963, that ampicillin trihydrate was also stable, but that discovery does not form part of the present invention.

Antibacterial agents such as benzylpenicillin have proved highly effective in the past in the therapy of infections due to Gram-positive bacteria, but such agents suffer from the serious drawbacks of being ineffective against numerous strains of bacteria, e.g., most Gram-negative bacteria. The compound of the present invention is particularly useful in that it possesses potent antibacterial activity against both Gram-positive and Gram-negative bacteria upon either parenteral or oral administration, and also exhibits resistance to destruction by acid.

D-(—)-α-Aminobenzylpenicillin, also known as D-6-(2-amino-2-phenyl-acetamido)penicillanic acid, 6-[D-(—)-α-aminophenyl-acetamido]penicillanic acid, and as ampicillin, is known in the technical literature, having been described, for example, in U.S. Pat. No. 2,985,648, the disclosure of which is incorporated herein by reference. According to the teachings of that patent, this penicillin is prepared by reaction of 6-amino-penicillanic acid with an acylating agent such as the acid chloride, acid bromide, acid anhydride, mixed anhydride, etc. of a derivative of D-(—)-α-aminophenylacetic acid in which the amino group is protected by a carbobenzoxy or other suitable protecting group. After completion of the acylation reaction, the protecting group is removed from the amino group such as by reduction with hydrogen in the presence of a catalyst. D-(—)-α-Aminobenzylpenicillin is also described in U.S. Pat. No. 3,140,282.

The known methods for the preparation of D-(—)-α-aminobenzylpenicillin by the acylation of 6-aminopenicillanic acid result in the preparation of aqueous mixtures which contain, in addition to the desired penicillin, unreacted 6-aminopenicillanic acid, hydrolyzed acylating agent, and products of side reactions such as the products of the acylating agent reacted with itself and/or with the desired penicillin, as well as other impurities. The D-(—)-α-aminobenzylpenicillin may then be recovered from the aqueous reaction mixture by concentration to small volume and recovering the product by filtration. The D-(—)-α-aminobenzylpenicillin is generally obtained in the form of a monohydrate, a dihydrate, or a mixture thereof. The monohydrates (as well as the dihydrates of D-(—)-α-aminobenzylpenicillin possess poor stability.

It is an object of this invention to provide a new form of D-(—)-α-aminobenzylpenicillin which possesses good stability upon storage.

This and other objects are achieved by the practice of this invention which comprises providing a new, stable crystalline form of D-(—)-α-aminobenzylpenicillin which is characterized by being substantially free of water in the chemically bound state, and by exhibiting an infrared absorption spectrum substantially as disclosed in FIG. 1 of the drawings. More specifically, this invention comprises providing a new crystalline form of D-(—)-α-aminobenzylpenicillin characterized by being substantially free of water in the chemically bound state, having a molecular weight of about 349, having an infrared spectrograph as disclosed in FIG. 1 of the drawings, and possessing substantially greater storage stability than hydrated crystalline D-(—)-α-aminobenzylpenicillin.

The anhydrous D-(—)-α-aminobenzylpenicillin of this invention may be obtained by suspending D-(—)-α-aminobenzylpenicillin·β-naphthalene sulfonate, also known as D-(—)-α-aminobenzylpenicillin·β-naphthalene sulfonic acid salt, in water and adjusting the pH of the suspension to about 6.0–8.0, and preferably 6.7–7.2, with triethylamine. The temperature of the suspension during the reaction is about 0°–75° C., and preferably 60–70° C. The adjustment of the pH causes precipitation of the Form II D-(—)-α-aminobenzylpenicillin to commence. Precipitation of the Form II D-(—)-α-aminobenzylpenicillin can be initiated if necessary by seeding. The pH of the solution is then adjusted to about 4.5–5.0 by the addition of an acid such as hydrochloric acid and cooled to complete precipitation. After precipitation of the Form II D-(—)-α-aminobenzylpenicillin is completed, it may be recovered by filtration. The product may then be washed with water and/or organic solvent such as methyl isobutyl ketone, and dried.

In carrying out the process at low temperatures, i.e., less than 60° C., it is essential that the D-(—)-α-aminobenzylpenicillin·β-naphthalene sulfonate suspension or solution does not become contaminated with particles of D-(—)-α-aminobenzylpenicillin hydrates. The hydrates act as seeds and cause the precipitation of D-(—)-α-aminobenzylpenicillin hydrates instead of Form II D-(—)-α-aminobenzylpenicillin.

While α-aminobenzylpenicillin can exist in two optically active isomeric forms [the D-(—)- and L-(+)-diastereoisomers], as well as the optically inactive DL form which is a mixture of the two optically active forms, the D-(—)- isomer being the most biologically active isomer, it has not as yet been determined whether the L-(+)- and DL forms can be prepared in crystalline form having the characteristics of Form II D-(+)-α-aminobenzylpenicillin. Therefore, the invention described and exemplified herein has been directed only to the D-(—)- isomeric form of α-aminobenzylpenicillin.

The D-(—)-α-aminobenzylpenicillin·β-naphthalene sulfonate used in the process for preparing the compound of this invention is prepared by contacting an aqueous solution of D-(—)-α-aminobenzylpenicillin, such as an impure aqueous solution containing D-(—)-α-aminobenzylpenicillin obtained as described in U.S. Pat. No. 2,985,648, with a β-naphthalene sulfonic acid.

After reaction, the D-(—)-α-aminobenzylpenicillin·β-naphthalene sulfonate precipitates and is recovered.

The novel crystalline form of D-(—)-α-aminobenzylpenicillin of this invention has a molecular weight of about 349, and is free or substantially free of water in the chemically bound state, containing less than about 1.8% water, and for that reason has been designated Form II D-(—)-α-aminobenzylpenicillin or Form II ampicillin. Form II is characterized by its distinct crystal structure as demonstrated by its infrared spectrum, an example of which is shown in FIG. 1 of the drawings. Form II D-(—)-α-aminobenzylpenicillin is readily distinguished from the D-(—)-α-aminobenzylpenicillin described in U.S. Pat. No. 2,985,648, and herein designated Form I, an example of the infrared spectrum of which is shown in FIG. 2 of the drawings, by comparing the infrared spectrum of FIG. 1 with that of FIG. 2. The novel crystalline form of ampicillin of this invention is further characterized by the fact that it may be stored for long periods of time without substantial potency loss. The novel crystalline form of ampicillin has been found to possess substantially greater storage stability than hydrated crystalline D-(—)-α-aminobenzylpenicillin, i.e., mono- and dihydrates of D-(—)-α-aminobenzylpenicillin.

The peaks at 2530, 1429 and 1009 cm$^{-1}$ in the infrared absorption spectra of FIGS. 1 and 2 are artificial and caused by operations within the infrared spectrophotometer, and therefore do not constitute a part of either infrared absorption spectrum.

The following examples will illustrate the present invention described herein without unduly restricting it.

EXAMPLE 1

A reaction mixture containing α-aminobenzylpenicillin, formed by the acylation of 1 kg. of 6-aminopenicillanic acid, is concentrated at less than 40° C. to about 15 liters. Methyl isobutyl ketone (7.5 liters) is added to the concentrate which is then chilled to 0°–5° C., adjusted to pH 1.8–2.0, agitated about five minutes, the resulting emulsion filtered, and the filtrates collected. The filter cake is washed with 2 liters of cold water, and then with 2.5 liters of methyl isobutyl ketone, and these wash portions are combined with the filtrate. The aqueous layer and the methyl isobutyl ketone layer of the filtrate are then separated, and the organic solvent layer is discarded. The aqueous layer is adjusted to pH 4–5 with triethylamine, maintained at 0°–10° C., and mixed with 7.5 liters of methyl isobutyl ketone. To the resulting mixture there is added with vigorous agitation 3 liters of an aqueous solution containing 1.35 kg. of β-naphthalene sulfonic acid. During addition of the β-naphthalene sulfonic acid, the reaction mixture is not allowed to exceed 10° C., and the pH is maintained above 1.5 by intermittent addition of triethylamine as required. Following the addition of the acid solution, the pH of the reaction mixture is adjusted to 1.6–2.0, seeded, and agitated for 2–4 hours at 0°–5° C., and at a pH of 1.6–2.0, whereupon α-aminobenzylpenicillin.β-naphthalene sulfonic acid salt precipitates. After precipitation of the product is completed, the reaction mixture is filtered, and the collected product washed twice with 2.5 liters of cold water and with three successive washes of 2.5 liters of methyl isobutyl ketone. The collected product, the monohydrate of β-naphthalene sulfonic acid salt of β-aminobenzylpenicillin is dried at 50° C., and found by bioassay to have 600 mcg. β-aminobenzylpenicillin activity/mg.

A 200 gm. portion of β-aminobenzylpenicillin.β-naphthalene sulfonic acid salt (prepared as described above) is added with agitation to 1500 ml. of water at room temperature. Triethylamine (54 ml.) is added to the resulting suspension over a period of several minutes. Four successive 200 gm. portions of the salt are added to the suspension, each portion being followed by the addition of 54 ml. triethylamine, and by agitation. Some pure β-aminobenzylpenicillin crystallizes out of the solution following each addition. The resulting slurry is agitated at room temperature (25°–30° C.) at a pH of 6.7–7.5 for about 1 hour. Subsequently the slurry is chilled, and, while chilling, the pH is slowly adjusted over about a 10–30 minute period to about 4.5–4.6 by the addition of about 45 ml. of 6N hydrochloric acid. After the pH is adjusted, the slurry is agitated at 0°–5° C. for about 2 hours, and then filtered. The mother liquors are removed from the collected solids which are then washed with two 200 ml. portions of ice water and then with 1000 ml. of cold methyl isobutyl ketone. After washing, the collected product, α-aminobenzylpenicillin, is dried at 50° C., and found to weigh about 415 gm., and to assay 1000 mcg. α-aminobenzylpenicillin/mg. (100% of theoretical activity; 70% of theoretical yield).

This crystalline product is designated Form II D-(—)-α-aminobenzylpenicillin, and is characterized by being substantially free of water in the chemically bound state, having a molecular weight of about 349, having an infrared absorption spectrum substantially as disclosed in FIG. 1 of the drawings, and possessing greater storage stability than Form I D-(—)-α-aminobenzylpenicillin.

EXAMPLE 2

To water (5950 ml.) there was added with stirring 792 gm. D-(—)-α-aminobenzylpenicillin.β-naphthalene sulfonate and 214 ml. triethylamine. The additions were repeated three more times with 10-minute intervals between additions, giving a total addition of 3168 gm. D-(—)-α-aminobenzylpenicillin.β-naphthalene sulfonate and 856 ml. triethylamine. After stirring for 1½ hours, the pH was adjusted to 4.6 with 120 ml. 37–38% HCl, and then the aqueous solution was cooled to 0' C., causing crystals to form. After 2 hours, the crystals were separated by filtration, washed twice with 794-ml. portions of ice water, and thrice with 760-ml. portions of methyl isobutyl ketone giving 1.80 kg. of wet cake. The wet cake dried at 120° F. for 21 hours.

The dried crystalline Form II D-(—)-α-aminobenzylpenicillin product (1.12 kg.) obtained, was found to contain 0.7% water, to bioassay 1010 mcg. D-(—)-α-aminobenzylpenicillin/mg., and to have the infrared absorption spectrum disclosed in FIG. 1 of the drawings.

EXAMPLE 3

A comparison of the stability of Form II D-(—)-α-aminobenzylpenicillin was made with that of Form I D-(—)-α-aminobenzylpenicillin. Samples of Form II D-(—)-α-aminobenzylpenicillin (product of Example 2) and Form I D-(—)-α-aminobenzylpenicillin were placed in snap-cap vials and stored at 56° C. The potency of each sample was determined by bioassay before and after storage. The moisture content of each sample was determined by Karl Fischer analysis before storage. Sample 1 is Form II and Samples 2–5 are Form I D-(−)-α-aminobenzylpenicillin.

The test data are presented in the table below.

TABLE

| | | POTENCY STABILITY AT 56° C. | | | | |
|---|---|---|---|---|---|---|
| | | Bio-assay Mcg./mg. | | | % Loss in Potency | |
| | % Mois- | Orig- | Months | | Months | |
| Sample | ture | inal | 1 | 2 | 1 | 2 |
| 1 | 1.1 | 1000 | 990 | 1040 | 1 | +3.5 |
| 2 | 3.7 | 920 | 640 | 450 | 30 | 51 |
| 3 | 4.8 | 940 | 580 | | 38.5 | |
| 4 | 5.2 | 960 | 620 | 480 | 35.5 | 50 |
| 5 | 6.5 | 955 | 500 | | 51 | |

It is apparent from the table that Form II D-(−)-α-aminobenzylpenicillin (Sample 1) was more stable upon storage than Form I D-(−)-α-aminobenzylpenicillin (Samples 2–5).

While this invention has been described and exemplified in terms of its preferred embodiment, those skilled in the art will appreciate that modifications can be made without departing from the spirit and scope of this invention.

We claim:

1. A new crystalline form of D-6-(2-amino-2-phenyl-acetamido)penicillanic acid characterized by being substantially free of water in the chemically bound state, having a molecular weight of about 349, having an infrared spectrograph as disclosed in FIG. 1 of the drawings, and possessing substantially greater storage stability than hydrated crystalline D-6-(2-amino-2-phenyl-acetamido)penicillanic acid.

2. The stable crystalline form of D-(−)-α-aminobenzylpenicillin which is characterized by being substantially free of water in the chemically bound state, and by exhibiting an infrared absorption spectrum substantially as disclosed in FIG. 1 of the drawings.

* * * * *

UNITED STATES PATENT OFFICE
CERTIFICATE OF CORRECTION

PATENT NO. : 3,941,773
DATED : March 2, 1976
INVENTOR(S) : Herbert H. Silvestri and David A. Johnson It is certified that error appears in the above-identified patent and that said Letters Patent are hereby corrected as shown below:

Column 3, line 69, "β-aminobenzylpenicillin" should read -- α-aminobenzylpenicillin --

Column 4, line 2, "β-aminobenzylpenicillin" should read -- α-aminobenzylpenicillin --

Column 4, line 3, "β-aminobenzylpenicillin." should read -- α-aminobenzylpenicillin. --

Column 4, line 11, "β-aminobenzylpenicillin" should read -- α-aminobenzylpenicillin --

Column 4, line 47, "0' C" should read -- 0° C --

Signed and Sealed this fifteenth Day of June 1976

[SEAL]

Attest:

RUTH C. MASON
Attesting Officer

C. MARSHALL DANN
Commissioner of Patents and Trademarks